United States Patent
Shalaby

(10) Patent No.: US 7,083,634 B2
(45) Date of Patent: *Aug. 1, 2006

(54) STABILIZED POLYESTER/CYANOACRYLATE TISSUE ADHESIVE FORMULATION

(75) Inventor: Shalaby W. Shalaby, Anderson, SC (US)

(73) Assignee: Poly Med Inc, Anderson, SC (US)

( * ) Notice: Subject to any disclaimer, the term of this patent is extended or adjusted under 35 U.S.C. 154(b) by 420 days.

This patent is subject to a terminal disclaimer.

(21) Appl. No.: 10/300,076

(22) Filed: Nov. 20, 2002

(65) Prior Publication Data

US 2003/0069535 A1  Apr. 10, 2003

Related U.S. Application Data

(60) Continuation-in-part of application No. 09/932,628, filed on Aug. 17, 2001, now Pat. No. 6,723,114, which is a division of application No. 09/439,167, filed on Nov. 12, 1999, now Pat. No. 6,299,631.

(60) Provisional application No. 60/115,836, filed on Jan. 14, 1999, provisional application No. 60/102,868, filed on Nov. 12, 1998.

(51) Int. Cl.
*A61B 17/08* (2006.01)

(52) U.S. Cl. ............ 606/213; 525/308; 424/78.27

(58) Field of Classification Search ........... 525/308; 606/214; 427/78.24
See application file for complete search history.

(56) References Cited

U.S. PATENT DOCUMENTS

| 3,221,745 A | 12/1965 | Coover, Jr. et al. | 128/334 |
| 3,223,083 A | 12/1965 | Cobey | 128/92 |
| 3,264,249 A | 8/1966 | Araki et al. | 260/32.4 |
| 3,559,652 A | 2/1971 | Benitt | 128/334 |
| 5,350,798 A | 9/1994 | Linden et al. | 525/41 |
| 5,422,068 A | 6/1995 | Shalaby et al. | 422/22 |
| 5,491,198 A | 2/1996 | Shalaby et al. | 525/340 |
| 5,558,517 A | 9/1996 | Shalaby et al. | 433/201.1 |
| 5,612,052 A | 3/1997 | Shalaby | 424/426 |
| 6,299,631 B1 | 10/2001 | Shalaby | 606/214 |
| 6,413,539 B1 | 7/2002 | Shalaby | 424/426 |
| 6,462,169 B1 | 10/2002 | Shalaby | 528/354 |
| 6,467,169 B1 | 10/2002 | Wieres | 29/890 |
| 6,699,940 B1 * | 3/2004 | Shalaby | 525/308 |
| 2004/0199207 A1 * | 10/2004 | Shalaby et al. | 606/214 |

FOREIGN PATENT DOCUMENTS

WO  WO0009166  *  2/2000

OTHER PUBLICATIONS

Shalaby, *Encyclopedia of Pharmaceutical Technology,* Swarbrick and Boylan, Eds., Marcel Dekker, Inc., New York, 1988, pp. 465-476.

* cited by examiner

*Primary Examiner*—Gary Jackson
(74) *Attorney, Agent, or Firm*—Leigh P Gregory

(57) ABSTRACT

The present invention is directed to adhesive/hemostatic formulations of 2-alkoxyalkyl cyanoacrylate, an absorbable liquid or solid polymeric modifier, and a general stabilizer against premature anionic polymerization of cyanoacrylates. The present adhesive formulations are useful as tissue adhesives/sealants, hemostatic agents, or as a means of patching and anastomotic coupling of damaged organs.

12 Claims, No Drawings

STABILIZED POLYESTER/CYANOACRYLATE TISSUE ADHESIVE FORMULATION

This is a continuation-in-part application of U.S. Ser. No. 09/932,628, filed Aug. 17, 2001 now U.S. Pat. No. 6,723,114, which is a divisional application of U.S. Ser. No. 09/439,167, filed Nov. 12, 1999, now issued as U.S. Pat. No. 6,299,631, which claimed the benefit of two provisional applications, U.S. Ser. No. 60/102,868, filed Nov. 12, 1998, and U.S. Ser. No. 60/115,836, filed Jan. 14, 1999.

BACKGROUND OF THE INVENTION

The prior art on absorbable alkoxyalkyl cyanoacrylate-based tissue adhesive/sealant formulations dealt with polymeric modifiers such as oxalate polymers of trimethylene glycol (U.S. Pat. No. 5,350,798), oxalate polymers of polyethylene glycol (U.S. Pat. No. 6,299,631), and trimethylene carbonate-based polymers (U.S. Pat. No. 6,299,631). All of these formulations were shown to exhibit clinically significant properties. However, it has been noted that upon packaging these formulations in market-acceptable and user friendly forms, occasional premature anionic polymerization of the cyanoacrylate component, and subsequent reduction or loss of these intended properties can be encountered in the presence of a trace amount of water or basic compounds that may be brought into contact with said formulations, inadvertently. Obviously, this can compromise the shelf-stability of the respective tissue adhesive/sealant in the final marketable form. Accordingly, this invention deals with the prevention of premature anionic polymerization and reduction or loss of intended adhesive/sealant properties by the incorporation of certain stabilizers into the absorbable cyanoacrylate formulation. The use of such stabilizers can also be extended to non-absorbable cyanoacrylate adhesives. Addition of such stabilizer is intended to achieve adequate shelf-stability of packaged products as well as to prevent any changes in the formulations during their preparation due to extraordinary exposure to water vapor or a similar anionic initiator.

SUMMARY OF THE INVENTION

The principle aspect of this invention is directed to a bioabsorbable adhesive formulation, which is an admixture of an alkoxyalkyl cyanoacrylate, an absorbable liquid or solid polymeric modifier, and a stabilizer against premature anionic polymerization of the cyanoacrylate components, wherein said stabilizers are one or more miscible acidic compounds, including either phosphorus-containing acids and precursors thereof such as pyrophosphoric acid, polyphosphoric acid, and phosphoric acid, or monobasic organic sulfonic acids such as p-toluene sulfonic acid, trifluoroacetic acid, and methanesulfonic acid at a concentration exceeding 1 ppm. The absorbable polymeric liquid or solid modifier can be one or more of the polymers described in U.S. Pat. Nos. 5,350,798 and 6,299,631.

DESCRIPTION OF THE PREFERRED EMBODIMENTS

This invention deals with absorbable tissue adhesive/sealant formulations that are stabilized against premature anionic polymerization based on combinations of 2-cyanoacrylate ester and one or more absorbable liquid or compliant solid copolyester modifier of the types disclosed in U.S. Pat. Nos. 5,350,798 and 6,299,631, in the presence of one or more miscible acidic compounds or precursors thereof including either phosphorus-containing compounds such as phosphoric acid, pyrophosphoric acid, and polyphosphoric acid, or monobasic organic sulfonic acids such as p-toluene sulfonic acid, methanesulfonic acid, trifluoroacetic acid, at a concentration that exceeds 1 ppm.

One specific aspect of this invention deals with adhesive/sealant formulations of 2-methoxypropyl cyanoacrylate and one or more amorphous or low-crystallinity polyaxial copolyesters, such as those described in U.S. Pat. No. 6,462,169 and pyrophosphoric acid as the stabilizer. Another specific aspect of this invention deals with adhesive/sealant formulations of 2-methoxypropyl cyanoacrylate and one or more absorbable, hydrogel-forming, self-solvating liquid copolyesters of those described in U.S. Pat. No. 6,413,539, after acylation of the hydroxyl end-groups of their chains and pyrophosphoric acid.

Another aspect of this invention deals with stabilized cyanoacrylates used as absorbable or non-absorbable tissue adhesives or as industrial adhesives, wherein the cyanoacrylate components can be one or a combination of these used as tissue adhesives/sealants or an industrial adhesive and the stabilizer being one or more of the acidic compounds or a precursor of acidic compounds. Among cyanoacrylate formulations suitable for stabilization are those comprising methyl cyanoacrylate, ethyl cyanoacrylate, isopropyl cyanoacrylate, n-propyl cyanoacrylate, n-butyl cyanoacrylate, isobutyl cyanoacrylate, isooctyl cyanoacrylate, and n-octyl cyanoacrylate.

Another aspect of this invention deals with minimizing or eliminating the chance of premature polymerization of cyanoacrylates or their formulations upon transfer to the application site during their use in a typical industrial application or use as tissue adhesives/sealants, wherein stabilization against premature polymerization is achieved through modifying the surface of the delivery apparatus in direct contact of the cyanoacrylate. A more specific aspect of this invention deals with a polymeric catheter or container made of polyethylene, polypropylene, or any similar polymer capable of surface sulfonation or phosphonylation to introduce covalently bonded acid groups on the cyanoacrylate-contacting surface as described in U.S. Pat. Nos. 5,558,517 and 5,491,198. Accordingly, the delivery device used to administer the cyanoacrylate-based system will be phosphonylated or sulfonated to introduce covalently bonded sulfonic or phosphonic groups on the contacting surface that will prevent premature anionic polymerization of the cyanoacrylate components. Another aspect of this invention deals with radiochemical sterilization (described in U.S. Pat. No. 5,422,068) of packaged cyanoacrylate formulations using a combination of 5 to 7.5 kGy of gamma radiation and radiolytically generated gaseous formaldehyde, wherein the liquid formulation is contained in an ampoule with a tapered neck made of a suitable polymer, such as polyethylene and enclosed in a hermetically sealed, secondary package containing a gas permeable fabric pouch containing radiolytically labile polyformaldehyde (as a precursor of formaldehyde). Radiochemically sterilized cyanoacrylate formulations, such as that of methoxypropyl cyanoacrylate, containing an absorbable copolyester modifier and stabilized against premature polymerization were shown to be fully sterile and, hence, suitable for internal surgical applications. Another aspect of this invention is a method of delivering radiochemically sterilized cyanoacrylate formulation for internal or external applications at surgical or wound repair sites. Another aspect of this invention is the use of radiochemically sterilized cyanoacrylate formulation endoscopically through polymeric delivery catheters or devices whose cyanoacrylate-contacting surface is chemically modified to introduce an acid group, such as phosphonic or sulfonic ones.

Another aspect of this invention deals with a cyanoacrylate-based composition colored with an organic dye.

Further illustrations of the present invention are provided by the following examples, which deal with the preparation of typical polymeric modifiers and their incorporation in tissue adhesive formulations with different cyanoacrylates in the presence of small amounts of polyphosphoric acid (PPA) as the stabilizer.

EXAMPLE 1

Preparation of a Polyethylene Glycol Copolyester (GF) Acetylated Derivative (AC-GF)

A copolyester of polyethylene glycol 400 (PEG-400) was prepared by end-grafting the PEG-400 (15 g) with a 60/40 molar ratio of dl-lactide/glycolide (85 g) at 150° C. in the presence of a catalytic amount of stannous octanoate until practically complete conversion is achieved. The resulting GF was isolated, purified, and characterized as described in U.S. Pat. No. 6,413,539. The purified product was then acylated by treating with a four-fold excess (based on $M_n$ determined by GPC) of acetic anhydride at 120° C. for four hours. Unreacted anhydride and the acetic acid by-product were removed by distillation under reduced pressure above 80° C. The acetylated GF (AC-GF) was characterized for identity (IR and NMR) and molecular weight (GPC).

EXAMPLE 2

Preparation and Characterization of Polyaxial Copolyester (PAX)

A polyaxial polymeric initiator was first prepared by copolymerization of 5/20/25 (molar) of glycolide (G), ε-caprolactone (CL), and trimethylene carbonate (TMC) in the presence of stannous octoate and trimethyl propane as a catalyst and monomeric initiator, respectively, as described in U.S. Pat. No. 6,462,169. The polyaxial polymeric initiator was then grafted with 1-lactide (LL) to yield a segmented, partially crystalline polymer comprising sequences derived from G, CL, TMC, and LL at a ratio of 5/20/25/50. The segmented copolymer was isolated and purified as per U.S. Pat. No. 6,467,169, and then characterized for identity (IR and NMR) molecular weight (GPC) and thermal properties (DSC).

EXAMPLE 3

Preparation of an 85/15 Tissue Adhesive Formulations of Undyed Methoxypropyl Cyanoacrylate (MPC) and AC-GF In a predried glass reactor equipped for mechanical stirring, AC-GF (5.3 g from Example 1), and an equal amount of MPC (5.3 g) containing small amounts of pyrophosphoric acid (2 mg), were mixed under a dry nitrogen atmosphere. The mixture is then heated to 110° C. and maintained at that temperature until complete mixing is achieved. The mixture was then cooled to 60° C. and an additional amount of MPC (24.7 g) was added and the mixing continued for about one hour and then allowed to reach room temperature to yield a uniform clear liquid. This was characterized for identity by infrared and adhesive strength using the fabric peel test [as described by J. D. Kline et al., Sixth World Biomaterials Congress, Trans. Soc. Biomat., III, 1062 (2000)].

EXAMPLE 4

Preparation of Dyed 85/15 Tissue Adhesive Formulation of MPC and AC-GF

This was conducted as in Example 3 with the exception of mixing D & C Violet #2 at 0.05% concentration with the final liquid formulation.

EXAMPLE 5

Preparation of Undyed Tissue Adhesive Formulations of 95/5, MPC and PAX

In a predried glass reactor equipped for mechanical stirring, PAX (20 g from Example 2) and MPC (20 g) containing a small amount of pyrophosphoric acid (8 mg) were mixed under a dry nitrogen atmosphere. The mixture is then heated to 110° C. and maintained at that temperature until complete mixing is achieved. The mixture was then cooled to 60° C. and an additional amount of MPC (360 g) was added and the mixing continued for about one hour and allowed to cool to room temperature to yield a uniform clear liquid. The product was characterized as described in Example 3.

EXAMPLE 6

Preparation of Dyed 95/5, MPC/PAX Formulation

This was conducted as in Example 5 with the exception of mixing D & C Violet #2 t 0.05% concentration with the final liquid formulation.

EXAMPLE 7

Preparation of Undyed 97/3, MPC/PAX Adhesive Formulation

This was conducted as in Example 5 with the exception of using 7.5 g of PAX (from Example 2) and 7.5 g of MPC containing 2.5 mg pyrophosphoric acid in the first stage, and 235 g of MPC in the second stage.

EXAMPLE 8

Packaging and Sterilization of Undyed 97/3, MPC/PAX

Polyethylene ampoules with tapered nicks were filled under dry nitrogen with undyed aliquots (0.2 ml) of the formulation from Example 7. Eighteen of these ampoules were packaged under dry nitrogen atmosphere in a hermetically sealed secondary package containing a porous, heat-sealed polyester pouch containing 200 mg of unstabilized polyformaldehyde powder (Celcon M-90). The secondary package and its contents were radiochemically sterilized using 5 kGy at a dose rate of 32 kGy/hour. The sterilized formulation was tested for identity (by IR), adhesive property (using the fabric peel test as in Example 3), and for sterility. Using standard microbiological assays, the liquid formulation and the surface of the sealed ampoule were tested after more than one month post-irradiation, and were shown to be sterile. The adhesive strength of the sterilized formulation was slightly lower than that of the same formulation before sterilization.

EXAMPLE 9

Preparation of Undyed 97/3 Tissue Adhesive Formulations of Ethyl Cyanoacrylate (EC) and AC-GF This was conducted as in Example 7 with the exception of using ethyl cyanoacrylate instead of MPC.

EXAMPLE 10

Evaluation of Shelf-Life Stability of Stabilized Cyanoacrylate Formulations

The shelf stability at 4° C. of the formulations of Examples 3 through 9 at 3, 6, 9, or 12 months were tested in terms of changes in typical group frequencies (using IR) and adhesive strength (using the fabric peel test). No discernable changes in properties were observed for all formulations, which exhibited acceptable one-year shelf stability.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A stabilized cyanoacrylate-based composition comprising methoxypropyl cyanoacrylate admixed with a liquid or compliant solid copolyester and at least about 1 ppm of a physically compatible acid comprising pyrophosphoric acid, wherein the acid stabilizes the reactive double bond of the cyanoacrylate against premature anionic polymerization.

2. A cyanoacrylate-based composition as in claim 1 wherein the acid comprises a phosphorous-containing acid selected from the group consisting of phosphoric acid, phosphorous acid anhydride, pyrophosphoric acid, and polyphosphoric acid.

3. A cyanoacrylate-based composition as in claim 1 wherein the acid comprises an organic sulfonic acid-based moiety selected from the group consisting of p-toluene sulfonic acid, methane sulfonic acid, and trifluoroacetic acid.

4. A cyanoacrylate-based composition as in claim 1, comprising methoxypropyl cyanoacrylate admixed with a liquid or compliant solid copolyester modifier and comprising pyrophosphoric acid as the stabilizer.

5. A cyanoacrylate-based composition as in claim 1, that is radiochemically stabilized and suitable for use as an absorbable, sterile, tissue adhesive or sealant in repairing internal wound or redirecting the function of internal organs.

6. A cyanoacrylate-based composition as in claim 5, that can be applied to surgically, accidentally, or pathologically compromised skin or internal sites using a delivery device or catheter having covalently linked acidic groups.

7. A cyanoacrylate-based composition as in claim 6, used in wound repairs associated with endoscopic procedures.

8. A cyanoacrylate-based composition as in claim 1, comprising at least one alkyl cyanoacrylate monomer selected from the group consisting of methyl-cyanoacrylate, ethyl-cyanoacrylate, n-propyl-cyanoacrylate, isopropyl-cyanoacrylate, n-butyl-cyanoacrylate, isobutyl-cyanoacrylate, isooctyl-cyanoacrylate, and n-octyl-cyanoacrylate.

9. A cyanoacrylate-based composition as in claim 8, that is radiochemically sterilized and packaged as a sterile product.

10. A cyanoacrylate-based composition as in claim 9, for use as a tissue adhesive, sealant, or blocking agent.

11. A cyanoacrylate-based composition as in claim 8 for use as an intravascular sealant or blocking agent, wherein its delivery system comprises an intravascular flexible catheter having covalently bound sulfonic groups on its surface.

12. A cyanoacrylate-based composition as in claim 9 for use as an intravascular sealant or blocking agent, wherein its delivery system comprises an intravascular flexible catheter having covalently bound sulfonic groups on its surface.

* * * * *